United States Patent [19]
Brown et al.

[11] Patent Number: 6,090,245
[45] Date of Patent: Jul. 18, 2000

[54] PROCESS FOR THE PURIFICATION OF MALEIC ANHYDRIDE

[75] Inventors: Henry C. Brown; William H. Alumbaugh, both of Pensacola, Fla.; Joseph C. Burnett, Austin, Tex.

[73] Assignee: Huntsman Petrochemical Corporation, Austin, Tex.

[21] Appl. No.: 09/273,173

[22] Filed: Mar. 19, 1999

Related U.S. Application Data

[62] Division of application No. 09/006,132, Jan. 13, 1998, Pat. No. 5,972,174.

[51] Int. Cl.$^7$ ........................................ B01D 3/34
[52] U.S. Cl. ............................... 203/49; 549/262
[58] Field of Search ............... 549/262; 203/50, 203/49

[56] References Cited

U.S. PATENT DOCUMENTS

| | | | |
|---|---|---|---|
| 2,095,578 | 10/1937 | Theiler | 203/49 |
| 2,848,460 | 8/1958 | Cummings | 549/262 |
| 3,818,680 | 6/1974 | Marquis | 55/48 |
| 3,850,758 | 11/1974 | Smith et al. | 203/38 |
| 3,865,849 | 2/1975 | Garkisch et al. | 260/346.8 M |
| 3,873,577 | 3/1975 | Garkisch et al. | 260/346.8 M |
| 3,939,183 | 2/1976 | Gardner et al. | 260/346.8 M |
| 3,965,123 | 6/1976 | Franklin | 260/346.8 M |
| 3,975,408 | 8/1976 | Boyer et al. | 260/346.8 R |
| 4,219,388 | 8/1980 | Heller et al. | 203/61 |
| 4,260,546 | 4/1981 | Schroeder et al. | 260/346.76 |
| 4,263,211 | 4/1981 | Keunecke et al. | 260/346.76 |
| 4,282,013 | 8/1981 | Franklin et al. | 55/48 |
| 4,358,600 | 11/1982 | Kuhlmann et al. | 549/262 |
| 4,568,427 | 2/1986 | Danz et al. | 203/57 |
| 4,681,046 | 7/1987 | Scharf et al. | 110/346 |
| 4,709,057 | 11/1987 | Sumida et al. | 549/262 |
| 4,921,977 | 5/1990 | Michl et al. | 549/256 |
| 4,961,827 | 10/1990 | Zimmerling et al. | 203/87 |
| 5,026,876 | 6/1991 | Sugawara et al. | 549/257 |
| 5,319,106 | 6/1994 | Kwon et al. | 549/262 |
| 5,631,387 | 5/1997 | Brown et al. | 549/259 |

FOREIGN PATENT DOCUMENTS

| | | | |
|---|---|---|---|
| 0 612 714 | 8/1994 | European Pat. Off. | 57/145 |
| 851570 | 10/1960 | United Kingdom . | |
| 869297 | 5/1961 | United Kingdom | 549/262 |
| 1 291 354 | 10/1972 | United Kingdom | 51/32 |
| 1 593 610 | 7/1981 | United Kingdom | 307/32 |

OTHER PUBLICATIONS

Weissberger, Technique of Organic Chemistry vol. III Part I, Separation and Purification, Interscience, pp. 818–819, 1956.

Webster's Seventh New Collegiate Dictionary, G. and C. Merriam Co., p. 837, 1965.

*Primary Examiner*—Bernard Dentz
*Attorney, Agent, or Firm*—Senniger, Powers, Leavitt & Roedel

[57] ABSTRACT

Processes for the purification and color stabilization of crude maleic anhydride by distillation in a batch or continuous distillation column.

8 Claims, 2 Drawing Sheets

PROCESS FOR THE PURIFICATION OF MALEIC ANHYDRIDE

This application is a Division of Ser. No. 09/006,132, filed Jan. 13, 1998, now U.S. Pat. No. 5,972,174.

BACKGROUND OF THE INVENTION

The present invention relates to the purification of maleic anhydride recovered from a gaseous reaction mixture produced by the catalyzed partial oxidation of a hydrocarbon. More particularly, the present invention is directed to processes and apparatus for improving the purity and color stability of recovered maleic anhydride.

Maleic anhydride is used alone or in combination with other acids in the manufacture of alkyd and polyester resins. It is also a versatile intermediate for chemical synthesis.

Maleic anhydride is prepared commercially by contacting a feed gas comprising molecular oxygen and a suitable hydrocarbon (e.g., n-butane or butene) with a vanadium-phosphorus-oxygen fixed-bed catalyst. The hydrocarbon is partially oxidized as it passes through a tubular reactor containing the fixed bed catalyst. The reaction product gas that is produced contains maleic anhydride together with oxidation by-products such as carbon monoxide, carbon dioxide, water vapor, acrylic and acetic acids and other by-products, along with inert gases present in air when air is used as the source of molecular oxygen.

The prior art discloses a number of methods for isolating and recovering maleic anhydride from the reaction product gas. The preferred method of recovery involves selectively absorbing maleic anhydride in a suitable solvent and then stripping the maleic anhydride from the resulting absorption liquor to obtain a crude maleic anhydride product as described in copending U.S. patent application Ser. No. 08/406,674 (HTS 7798). In the process, the reaction product gas exits the reactor and is cooled to a temperature above the dew point of the water in the reaction product gas in a heat exchanger. The cooled product gas exiting the heat exchanger is introduced into an absorber column in which the gas is contacted with a lean maleic anhydride-absorbing solvent. The gas and solvent come into contact in an absorption zone containing either packing material or trays for promoting gas/liquid contact. Maleic anhydride is absorbed in the solvent along with a portion of the oxidation by-products (e.g., carbon monoxide, carbon dioxide, water, acrylic acid, acetic acid and polymeric tars). The remaining oxidation by-products and inert gases in the product gas pass from the system as an exhaust gas substantially free of maleic anhydride. The absorption liquor exits the absorber column and flows to a rich solvent surge tank.

The absorption liquor from the surge tank is continuously stripped of maleic anhydride in a stripping column to recover crude maleic anhydride and regenerated absorbing solvent containing the absorbing solvent and contaminants. In the stripper column, maleic anhydride and lower boiling materials of the absorption liquor (mostly water and acrylic acid) immediately vaporize. The vapor rises through the column, exits the top of the column and enters a stripper condenser in which the vapor is cooled to produce a condensate. All condensate formed in the stripper condenser is returned to the stripper column as reflux. A liquid side draw of crude maleic anhydride is continuously removed from the stripper column and forwarded to a maleic anhydride purification stage.

Crude maleic anhydride recovered in a process as described above is generally treated by introducing the crude maleic anhydride into a batch distillation column. The batch distillation process consists of a forecut step folowed by a heartcut step. In the forecut step, low boilers are removed at the top of the column and partially condensed. A portion of the condensate is returned to the column as reflux, and the remainder of the condensate is removed as a forecut. After removal of the forecut quantity, the heartcut step is conducted. In the heartcut step, vapor removed from the top of the column is condensed to form a condensate. A portion of the condensate is recycled back to the top of the column as reflux. The remainder is withdrawn as purified maleic anhydride product. The color stability of the maleic anhydride product is improved by increasing the volume of forecut removed from the column. However, removal of a greater volume of forecut reduces the throughput and yield of maleic anhydride product per batch.

U.S. Pat. No. 3,865,849 describes a two stage purification method in which maleic acid in crude maleic anhydride is thermally decomposed into maleic anhydride and water in the first stage, a forerun composed predominantly of water is separated in the first stage, and maleic anhydride is continuously distilled in the second stage. The first stage is carried out in a cascade with at least two reactors in series and a common distillation column operated at 200 mm Hg. Vapors from the reactors are directed to the base of the distillation column. Vapors containing water and low boiling impurities are removed from the top of the column and discharged after condensation as a forerun. After removal of the forerun, maleic anhydride vapors are removed from the top of the column, condensed and returned to the column. Maleic anhydride exiting the last reactor is continuously pumped to a distillation column operated at 60 mm Hg. Vapors withdrawn from the top of the column are condensed. A portion of the condensate is refluxed to the top of the column, and the remainder is withdrawn as purified maleic anhydride. The bottoms residue contains 20 wt. % fumaric acid and high boiling resinous components and 80 wt. % maleic acid. The maleic acid is recovered by distillation and recycled to the first reactor.

U.S. Pat. No. 3,939,183 describes distillation of crude maleic anhydride in a twenty tray distillation column operated at a pressure of about 50 torr and an overhead temperature of about 238° F., a forecut takeoff of 2.5–6% of charge, a heartcut takeoff of 75–85% of charge, and a 9:1 reflux ratio during heartcut takeoff. Improved color stability is obtained by contacting the crude maleic anhydride with a metal halide and phosphorus pentoxide or a perborate before distillation.

U.S. Pat. No. 3,965,123 describes a batch or continuous process for recovering maleic anhydride of good color stability. Crude maleic anhydride from a receiving vessel is introduced into the top of a lights stripper. Vapor taken overhead is recycled to the receiving vessel. Maleic anhydride condenses in the receiving vessel and is returned to the lights stripper. Vapor in the receiving vessel is partially condensed and light boiling materials, such as acetic acid and acrylic acid, are removed. The stripped maleic anhydride exits from the bottom of the stripper and is introduced into a twenty tray batch distillation column operating at 50 mm Hg and an overhead temperature of 238° F. The initial 90 wt % of the material distilled overhead is taken as a product cut. Alternatively, the first 5 wt. % is taken as a forecut and the next 85 wt. % of the overhead stream is taken as a product cut. In another embodiment, the crude maleic anhydride from the receiving vessel is fed directly to the distillation column, a 5 wt. % forecut is taken, and the next 85 wt. % of the overhead stream is taken as product. When manganous chloride is then added to the product and the product is heated at 284° F. for 24 hours, the maleic anhydride has a color of 10–50 Hazen. When manganous chloride is not added to the product, the maleic anhydride has the same or worse Hazen color than typical commercial maleic anhydride.

U.S. Pat. No. 4,260,546 describes a twenty tray batch distillation column whose trays have a separation efficiency of 50% at the conditions of 100 mm Hg absolute pressure, a 1% forecut takeoff and a 1:1 reflux ratio during heartcut takeoff.

U.S. Pat. No. 4,921,977 describes a process for improving the color stability of maleic anhydride by treating crude maleic anhydride with a gas containing oxygen before or during continuous or batch distillation. Crude maleic anhydride is introduced to the tenth plate of a 50 plate fractionating column having an 80 mm diameter and operating at a head pressure of 100 mbar. Vapor removed from the head is condensed and 99% is recycled to the column as reflux. The remaining 1% is removed as product containing 99.98% maleic anhydride. Liquid maleic anhydride taken from the fortieth plate initially has a platinum-cobalt color of 5–10 which increased to 40–60 after two days in storage. When the process is repeated with air being introduced into the crude maleic anhydride fed to the column, the platinum-cobalt color remains at 5–10 after storage.

U.S. Pat. No. 4,961,827 describes a process for preparing purified maleic anhydride having good color stability. Crude maleic anhydride is fed to the eighteenth bubble cap tray of an 80 mm diameter column containing sixty bubble cap trays operated under a head pressure of 150 mbar. Vapor containing low boilers removed from the top of the column is condensed and 99.5% of the condensate is recycled to the column as reflux. The remaining 0.5% of the condensate is product containing 99.97 wt. % maleic anhydride. Vapor taken off from the fiftieth tray is composed of 99.7 wt. % maleic anhydride and 0.3 wt. % citraconic anhydride. The vapor is passed to a condenser in which 2–10% of the gas is condensed as a precondensate. The remaining vapor is completely condensed downstream. The maleic anhydride has a color of less than 40 Hazen when heated at 140° C. for two hours. The precondensate has a color greater than 200 Hazen.

U.S. Pat. No. 5,319,106 describes a maleic anhydride purification process in which crude maleic anhydride is fed from a stripper to a light ends distillation column. A polymerization inhibitor is fed to the top of the column to inhibit polymerization of acrylic acid. Acrylic and acetic acids are distilled overhead and vented. The bottoms from the stripper are introduced into a product distillation column wherein a vapor is distilled off overhead and condensed to form a condensate. The noncondensables are vented, and the condensate is the maleic anhydride product. The bottoms from the column, which contain heavy ends, the polymerization inhibitor and organic solvent, are recycled to the stripper.

British Patent No. 1,291,354 describes purification of crude maleic anhydride by feeding the crude to the fifteenth tray of a distillation column having twenty trays operating at a pressure of 70 mm Hg. Purified maleic anhydride is removed as a vapor above the fifteenth tray. A forecut of about 0.5% of the crude is withdrawn at the top of the column.

European Patent Application No. 612,714 describes a continuous maleic anhydride purification process in which crude maleic anhydride is introduced into a first fractionating column wherein light boiling impurities are removed as an overhead vapor and liquid maleic anhydride is removed from the bottom of the column and directed to the center stage of a second fractionating column. The overhead vapor is partially condensed and the maleic anhydride condensate is totally recycled to the column. The uncondensed vapor containing maleic anhydride, water and coloring substances is partially condensed in a second condenser and the condensate is recycled upstream to the absorption tower or the first fractionating column. Purified maleic anhydride containing less than 0.01% acrylic acid and less than 0.05% maleic acid is recovered from a stage above the center stage of the column.

SUMMARY OF THE INVENTION

Among the objects of the present invention, therefore, are the provision of an improved process for the purification and recovery of maleic anhydride in which maleic anhydride is efficiently recovered by distillation; the provision of an improved process for the purification and recovery of maleic anhydride in which color precursors are separated from maleic anhydride to improve the color stability, purity and yield of the maleic anhydride; the provision of an improved process for the purification and recovery of maleic anhydride in which maleic anhydride throughput is improved and cycle time is reduced; the provision of an improved process for the purification and recovery of maleic anhydride which reduces the build-up of polymeric tars in the still pot of a batch distillation column; and the provision of an improved process for the purification and recovery of maleic anhydride which removes low and middle boiling materials and other impurities generated by decomposition of crude maleic anhydride during distillation.

Briefly, therefore, the present invention is directed to a process for the purification and color stabilization of crude maleic anhydride by distillation in a batch distillation column. The process includes heating crude maleic anhydride, removing a first forecut comprised of maleic anhydride and low boiling materials, removing an overhead vapor after removal of the first forecut, condensing at least a portion of the overhead vapor to an overhead condensate, directing at least a portion of the overhead condensate to the column as reflux, and withdrawing a heartcut comprising maleic anhydride from a stage below that at which the first forecut and the overhead vapor are removed. The low boiling materials have a boiling point between about 45° C. and about 155° C. at a pressure of 760 mm Hg. The overhead vapor is comprised of middle boiling materials including maleic anhydride, and the middle boiling materials have a boiling point between about 160° C. and about 285° C. at a pressure of 760 mm Hg. The heartcut is withdrawn during removal of the overhead vapor.

Another embodiment of the invention is directed to a process for the purification and color stabilization of crude maleic anhydride by continuous distillation. The process includes introducing crude maleic anhydride in a stripper column, removing an overhead stream from the stripper column, removing a bottoms stream from the stripper column, introducing the bottoms stream into a refining column, removing an overhead vapor from the refining column, condensing a portion of the overhead vapor to an overhead condensate, directing at least a portion of the overhead condensate to the refining column as reflux, and withdrawing a side draw stream comprising at least 99.90 wt. % maleic anhydride from the refining column during removal of the overhead vapor. The overhead vapor is comprised of middle boiling materials including maleic anhydride and has a boiling point between about 160° C. and about 285° C. at a pressure of 760 mm Hg.

The present invention is also directed to a process for the purification and color stabilization of crude maleic anhydride by continuous distillation The process includes heating crude maleic anhydride in a stripper column, removing an overhead stream from the stripper column, removing a bottoms stream from the stripper column, introducing the bottoms stream into a refining column, removing an overhead vapor from the refining column, condensing a portion of the overhead vapor to an overhead condensate, directing a portion of the overhead condensate to the refining column as reflux, removing the overhead condensate that is not directed to the refining column as reflux as an overhead distillate at a reflux to overhead distillate weight ratio between about 20:1 and about 500:1; and withdrawing a side draw stream comprising at least 99.5 wt. % maleic anhydride from the refining column during removal of the overhead vapor. The overhead vapor is comprised of middle boiling materials including maleic anhydride and has a boiling point between about 160° C. and about 285° C. at a pressure of 760 mm Hg.

Yet another embodiment of the invention is directed to a process for the purification of crude maleic anhydride by distillation including treating the crude maleic anhydride with a gas containing an inert gas and, optionally, oxygen, such that noncondensables are purged from the crude maleic anhydride when the ratio of millimoles of oxygen in the cumulative gas flow during distillation to moles of crude maleic anhydride initially charged to the column is up to about 3.5:1.

Another embodiment of the invention is directed to a process for the purification of crude maleic anhydride by distillation including treating the crude maleic anhydride with a gas containing an inert gas and up to 5 mol. % oxygen such that noncondensables are purged from the crude maleic anhydride.

Other objects and features of this invention will be in part apparent and in part pointed out hereinafter.

DETAILED DESCRIPTION OF THE PREFERRED EMBODIMENTS

In accordance with the present invention, a process for the purification and color stabilization of crude maleic anhydride is provided in which maleic anhydride is separated from low boiling and middle boiling materials by distillation. Low boiling and middle boiling materials and other impurities are present in crude maleic anhydride feed and are also generated as the result of chemical decomposition and other chemical transformations of the maleic anhydride during distillation. Middle boiling materials, such as alcohols, aldehydes and vinyl ethers, are generally difficult to separate from maleic anhydride and are believed to impair the color stability of maleic anhydride at concentrations of about 10 ppm or more. It has been discovered that separation is enhanced by removing a forecut comprised of maleic anhydride and low boiling materials from the upper portion of the column and subsequently removing a refined product comprised of maleic anhydride from a stage above the center stage of the column while an overhead vapor comprised of middle boiling materials including maleic anhydride is removed from the upper portion of the column and partially condensed. At least a portion of the overhead vapor condensate is directed to the column as reflux to provide liquid for vapor/liquid contact within the column. The remainder of the overhead vapor condensate, if any, is removed as an overhead distillate at a reflux to overhead distillate weight ratio between about 144:1 and about 2:1. It has been found that removing the overhead vapor and returning middle boiling materials to the upper portion of the column at a reflux ratio in this range results in removal of middle boiling materials in the overhead distillate. The process removes low boiling and middle boiling materials and other impurities present in the maleic anhydride feed or generated during distillation, thereby providing a greater yield of refined product that constitutes high purity maleic anhydride exhibiting enhanced color stability after stabilization.

For purposes of the present invention, low boiling materials have a boiling point between about 45° C. and about 155° C. at a pressure of 760 mm Hg, and middle boiling materials have a boiling point between about 160° C. and about 285° C. at a pressure of 760 mm Hg. A refined product is a product cut comprised of at least about 95.0 wt. % maleic anhydride, preferably at least 99.5 wt. %, and, more preferably, between about 99.90 wt. % and about 99.98 wt. %. The refined product is referred to as a heartcut in a batch distillation process and as a side draw stream in a continuous distillation process of the invention. A forecut or an overhead distillate enriched in low boilers is comprised of maleic anhydride and low boiling materials and is removed at a stage above that at which the heartcut or side draw stream is removed. An overhead distillate is a stream comprised of middle boiling materials including maleic anhydride that is removed at a stage above that at which the heartcut or side draw stream is removed.

It has also been found that purification of crude maleic anhydride is improved by treating the crude maleic anhydride with a gas comprising an inert gas and up to 5 mol. % oxygen in order to purge low boiling materials and noncondensables from the crude maleic anhydride into the lower portion of the distillation column. Oxygen within the sparge gas is believed to oxidize color forming materials within the crude maleic anhydride resulting in improved color stability.

Figure 1:
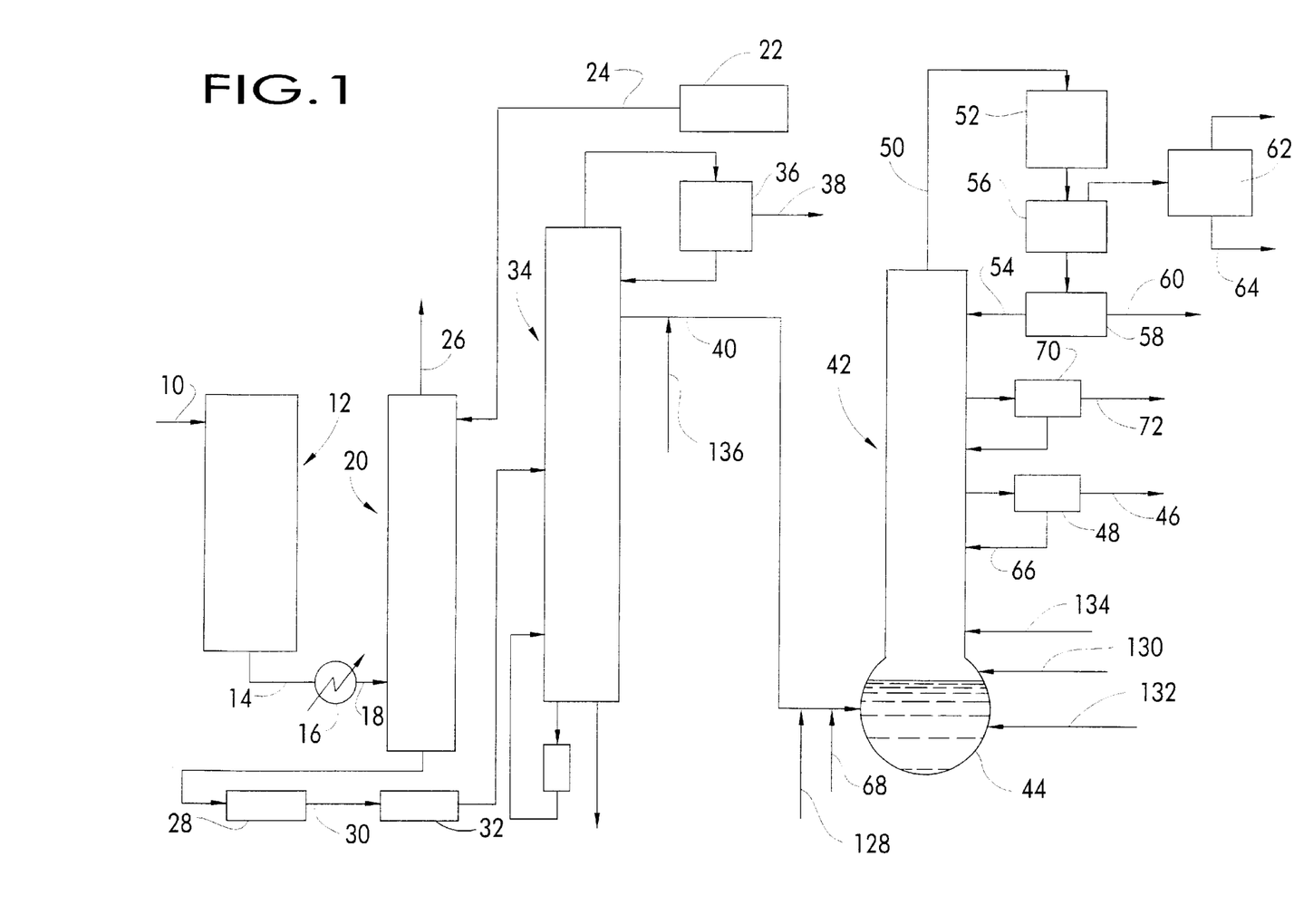
FIG. 1 is a schematic diagram of a process and apparatus for the purification and recovery of maleic anhydride via batch distillation in accordance with the present invention.

A schematic diagram of the process and apparatus of the present invention is illustrated in FIG. 1. The process includes the production of maleic anhydride, absorption of maleic anhydride in a solvent, and stripping maleic anhydride from the solvent as described in copending U.S. patent application Ser. No. 08/406,674 (HTS 7798). The maleic anhydride is then purified according to the present invention.

In order to produce maleic anhydride, a feed gas mixture comprising molecular oxygen and a suitable hydrocarbon is introduced via line 10 into a reactor 12 containing an oxidation catalyst for the partial oxidation of the hydrocarbon to form maleic anhydride. The feed gas mixture is produced by mixing a gas containing molecular oxygen, preferably air, and a gaseous hydrocarbon feedstock. Typically, the hydrocarbon is admixed with the molecular oxygen-containing gas at a concentration of about 1.5 mole percent to about 10 mole percent hydrocarbon. It is well known to those skilled in the art that a variety of hydrocarbons, such as n-butane, can be catalytically converted to maleic anhydride.

Hydrocarbons in the feed gas mixture are converted to maleic anhydride by contacting the feed gas mixture with a vanadium-phosphorus-oxygen catalyst at elevated temperatures in the reactor 12. A variety of reactor configurations can be used to produce a reaction product gas comprising maleic anhydride. Both fluidized bed reactors and fixed-tube, heat-exchanger type reactors are satisfactory. The details of the operation of these reactors are well known to those skilled in the art.

The feed gas mixture flows through the reactor in which it contacts the vanadium-phosphorus-oxygen catalyst. Typically, the feed gas mixture is contacted with the catalyst at a space velocity of about 100 hr$^{-1}$ to about 4,000 hr$^{-1}$ at a temperature from about 300° C. to about 600° C., preferably about 1800 hr$^{-1}$ and about 325° C. to about 500° C., to provide an excellent yield of and selectivity to maleic anhydride. Pressure is not critical to the oxidation reaction. The reaction may be conducted at atmospheric, superatmospheric, or subatmospheric pressures. For practical reasons, however, it will generally be preferred to conduct the reaction at or near atmospheric pressure. Generally, pressures from about 1.013×10$^2$ kPa absolute (14.7 psia, 1 atm.) to about 3.10×10$^2$ kPa absolute (45.0 psia) may be employed.

The reaction product gas typically contains about 0.5 to about 2 percent by volume maleic anhydride together with oxidation by-products such as carbon monoxide, carbon dioxide, water vapor, acrylic and acetic acids and other by-products, along with inert gases present in air when air is used as the source of molecular oxygen. It will be recognized by those skilled in the art that the type of maleic anhydride reactor, and the type and concentration of the hydrocarbon in the feed gas mixture will affect the concentrations of maleic anhydride and oxidation by-products in the reaction product gas withdrawn from the reactor.

The reaction product gas exits reactor 12 through line 14 and is directed to a heat exchanger 16 to cool the gas to a temperature preferably below about 200° C., but above the dew point of the water in the reaction product gas. If the product gas is cooled to a temperature below the dew point of water, maleic anhydride, or other components, these materials will accumulate on the walls of the equipment and obstruct gas flow. Generally, for a product gas containing about 1 volume percent maleic anhydride and about 10 volume percent water vapor, the product gas should be cooled to a temperature between about 60° C. and about 200° C., preferably between about 100° C. and about 150° C.

The cooled product gas exiting heat exchanger 16 flows via a rich gas line 18 to an absorber column 20 while lean maleic anhydride-absorbing solvent from lean solvent storage tank 22 flows via lean solvent line 24 and is introduced near the top of the column. The reaction product gas and the lean solvent flow countercurrently through absorber column 20. Suitable absorbing solvents, such as dibutyl phthalate, are well known in the art.

The absorption zone of the absorber column 20 comprises packing material (e.g., saddles, rings etc.) for promoting gas/liquid contact and mass transfer of maleic anhydride and a portion of the oxidation by-products (e.g., carbon monoxide, carbon dioxide, water, acrylic and acetic acids and polymeric tars) from the gas phase to the liquid phase. Alternatively, the absorber column may comprise a tray column in which gas/liquid contact is effected on the trays. The gas phase containing remaining oxidation by-products and inert gases is released through a vent line 26 at the top of absorber column 20 as an exhaust gas substantially free of maleic anhydride. The absorption liquor exits from a point near the bottom of the absorber column 20 and flows to a rich solvent surge tank 28.

In addition to absorbing solvent, maleic anhydride and oxidation by-products, the absorption liquor further comprises a variety of contaminants including maleic, fumaric and phthalic acids, polymeric tars, and phthalic anhydride that are generated in the absorption and stripping loop. Maleic acid is present as a result of the hydrolysis of maleic anhydride in the absorption liquor. Maleic acid subsequently isomerizes to produce fumaric acid. Phthalic anhydride is produced as a result of an ester exchange reaction between maleic anhydride and water and, when dibutyl phthalate is used as the absorbing solvent, is also produced as a result of hydrolysis or thermal decomposition of the solvent. Hydrolysis of phthalic anhydride produces phthalic acid in the absorption liquor.

The absorption liquor from the absorber column is continuously stripped of maleic anhydride in a stripping step to recover crude maleic anhydride and regenerated absorbing solvent comprising the absorbing solvent and contaminants. As shown in FIG. 1, the rich absorption liquor from surge tank 28 flows via line 30 to a stripper feed preheater 32 where it is heated before being introduced above a stripping zone of a stripper column 34. The absorption liquor introduced into the stripper column 34 is preferably above the bubble point at the prevailing pressure within the column such that maleic anhydride and lower boiling components of the absorption liquor (mostly water and acrylic acid) immediately vaporize. The vapor rising through the stripper column 34 exits the top of the column and enters a stripper condenser 36 which cools the vapor to produce a condensate. Uncondensed components of the vapor exit the stripper condenser 36 via line 38. All the condensate formed in the stripper condenser 36 is returned to the stripper column 34 as reflux and enters a rectifying zone of the stripper column.

A liquid side draw of crude maleic anhydride is continuously removed from the rectifying zone of the stripper column 34 via a chimney tray liquid trap at line 40. The crude product is forwarded to a maleic anhydride purification stage.

The liquid phase within the stripper column 34 flows downward from the column feed inlet through the stripping zone and circulates through a stripper reboiler. A portion of the liquid returning from the reboiler vaporizes and flows upward through the stripping zone. Stripper bottoms are pumped to an afterflasher for regeneration of solvent and further removal of maleic anhydride. A portion of the afterflasher condensate flows to rich solvent surge tank 28. Operation of the reactor, absorber column and stripping column is described in copending U.S. patent application Ser. No. 08/406,674 (HTS 7798), which is incorporated herein by reference.

Maleic anhydride removed from the stripper column 34 is then purified by batch or continuous distillation. When purification is batch-wise, crude maleic anhydride is directed via line 40 to a batch refiner 42 for purification as shown in FIG. 1. Crude maleic anhydride is fed to a still pot 44 at the base of the batch refiner 42. The crude maleic anhydride is heated to a temperature between about 140° C. and about 190° C., preferably between about 160° C. and about 170° C., while the column is operated at a head pressure of about 185 to about 385 mm Hg, preferably from about 200 mm Hg to about 280 mm Hg. At these operating conditions, materials within the crude maleic anhydride decompose in the still pot 44 throughout the distillation and form low boiling materials. As vapor rich in the low boiling materials forms in the still pot, the vapor enters the column where it is brought into countercurrent contact with a descending stream of boiling liquid. The refiner 42 contains a packing material (e.g., saddles, rings etc.) for promoting vapor/liquid contact and mass transfer of maleic anhydride from the vapor phase to the liquid phase. Alternatively, the batch refiner 42 may comprise a tray column in which vapor/liquid contact is effected on perforated plates or trays.

The batch refiner 42 generally has between about 10 and about 50 equilibrium stages. The heartcut is withdrawn from a stage that is at least 8 equilibrium stages above the still pot 44. The refiner 42 generally includes between about 8 and about 48 equilibrium stages between the still pot 44 and a stage at which the heartcut is withdrawn, and between about 1 and about 20 equilibrium stages between the stage at which the heartcut is withdrawn and the top of the column. The heartcut is typically withdrawn via line 46 from a reflux splitter 48 located above the center stage of the column. Preferably, the batch refiner includes between about 10 and about 30 equilibrium stages between the still pot 44 and the reflux splitter 48, and between about 1 and about 8 equilibrium stages between the reflux splitter 48 and the top of the column. Although a refiner having more equilibrium stages will improve the selectivity and separation of components of the crude maleic anhydride, the cost of additional stages may not be justified by the additional degree of resolution achieved.

For purposes of the present invention, an equilibrium stage is a stage at which the vapor and liquid streams leaving the stage are in equilibrium with each other. An equilibrium stage in a plate column is known as a theoretical plate, while in a packed column it is known as a transfer unit. The actual stages in a column can be determined from the number of equilibrium stages by well known methods. The number of actual stages in a plate column is determined by dividing the number of theoretical plates by a plate efficiency. The height of packing needed to accomplish a separation in a packed column is determined by multiplying the number of transfer units (NTU) required times the height equivalent to one transfer unit (HTU).

Vapor rising within the upper portion of the batch refiner 42 is removed via line 50 and partially condensed at a temperature above the dew point of the water in the vapor in a condenser 52 to form a condensate. Initially, the condensate is directed to the refiner 42 as reflux via line 54.

After start-up of the refiner 42, an overhead vapor is removed at a stage above the stage at which the heartcut is withdrawn to purge impurities having a lower boiling point than maleic anhydride from the system. The overhead vapor is comprised of low boiling materials, which have a boiling point between about 45° C. and about 155° C. at a pressure of 760 mm Hg, and maleic anhydride. Preferably, the overhead vapor is removed at or near the top of the column. In FIG. 1, the overhead vapor is removed via line 50 from the top of the column.

The overhead vapor partially condenses in a condenser 52 at a temperature above the dew point of the water in the vapor to form an overhead vapor condensate. The condensate separates from remaining vapor in a separator 56. A reflux splitter 58 directs at least a portion of the overhead vapor condensate to the column as reflux via line 54, while the remainder of the overhead vapor condensate is removed as a first forecut via line 60. The weight ratio of reflux via line 54 to first forecut via line 60 is preferably between about 15:1 and about 1:2, more preferably between about 8:1 and about 4:1, and, most preferably, between about 6:1 and about 5:1.

The vapor leaving the separator 56 partially condenses in condenser 62 and is removed as a first forecut that is rich in low boilers via line 64. The first forecuts can then be recycled via lines 60 and 64 to the lean solvent storage tank 22 storing the lean maleic anhydride absorbing solvent to be fed to the absorber column 20, or to the surge tank 28 storing the rich absorption liquor to be fed to the stripper column 34.

After the forecut is removed from the batch refiner 42, the operating temperature and pressure of the column are reduced to between about 125° C. and about 155° C., preferably between about 130° C. and about 140° C., and about 50 mm Hg to about 185 mm Hg, preferably between about 80 mm Hg and about 100 mm Hg. Operation of the column at a higher temperature and pressure would increase the rate of tar and polymer formation in the still pot 44 resulting from thermal decomposition of crude maleic anhydride heated for a prolonged period. Column operation at an even lower temperature may cause maleic anhydride to solidify in the condenser 52.

After reducing temperature and pressure, a heartcut comprising maleic anhydride is withdrawn at a stage above the center stage of the batch refiner 42. A liquid stream leaving the column enters a product splitter 48 that directs a portion of the liquid stream to the column as reflux via line 66. The remainder of the liquid stream is removed via line 46 as heartcut. In an alternative embodiment, the heartcut is directly removed from the refiner 42 via line 46 without being directed through an external product splitter 48 because the liquid stream is split internally. In either embodiment, the weight ratio of the heartcut withdrawn from the column to remaining liquid travelling down the column from the stage at which the heartcut is withdrawn is preferably between about 4:1 and about 1:4, more preferably between about 3:1 and about 1:1, and, most preferably, between about 2.5:1 and about 2:1.

As the heartcut is withdrawn from the refiner 42, an overhead vapor comprised of middle boiling materials, including maleic anhydride, having a boiling point between about 160° C. and about 285° C. at a pressure of 760 mm Hg is removed at a stage above that at which the heartcut is withdrawn. Preferably, the overhead vapor is withdrawn at or near the top of the refiner 42 via line 50.

The overhead vapor is partially condensed in the condenser 52 to form an overhead vapor condensate. The condensate separates from remaining vapor in the separator 56. The reflux splitter 58 directs at least a portion of the overhead vapor condensate to the column as reflux via line 54, while the remainder of the overhead vapor condensate is removed as an overhead distillate via line 60. The weight ratio of reflux via line 54 to overhead distillate via line 60 is preferably between about 300:1 to about 50:1, more preferably between about 250:1 to about 75:1, and, most preferably between about 200:1 to about 100:1.

The vapor leaving the separator 56 condenses in the condenser 62 and is removed as an overhead distillate enriched in low boilers via line 64. The overhead distillate streams can be recycled via lines 60 and 64 to the lean solvent storage tank 22 storing the lean maleic anhydride absorbing solvent to be fed to the absorber column 20, to the surge tank 28 storing the rich absorption liquor to be fed to the stripper column 34, or via line 68 to the crude maleic anhydride feed to the batch refiner 42. The overhead distillate via line 60 can also be used as maleic anhydride product if the overhead vapor condensate is of the desired purity and is heat stable.

The volume of forecut plus overhead distillate removed from the column at line 60 is between about 1% and about 20% of the volume of crude maleic anhydride introduced into the still pot 44. Preferably, the volume of the forecut plus overhead distillate removed is between about 1% and about 10%. If the volume of forecut plus overhead distillate removed is greater than 20%, the maleic anhydride yield may be adversely effected.

The batch-wise process of the present invention serves to effectively separate middle boiling materials from maleic anhydride at the above-described reflux ratios to improve maleic anhydride yield and color stability. The heartcut contains at least about 95.0 wt. % maleic anhydride, preferably at least about 99.5 wt. %, and, more preferably, between about 99.90 wt. % and about 99.98 wt. % maleic anhydride. The heartcut generally has a boiling point between about 131° C. and about 133° C. at a pressure of about 85 mm Hg. Deleterious impurities in the heartcut are minimized by the process of the invention. The heartcut contains not more than 10 ppm acrylic acid and not more than about 0.02 wt. % maleic acid.

The overhead distillate streams via lines 60 and 64 can be removed during the entire period in which heartcut is withdrawn, or during a portion of the heartcut withdrawal period. Preferably, an overhead distillate is removed during the initial 50% of heartcut withdrawal. The overhead distillate via line 60 is more concentrated in middle boiling materials when the overhead distillate flow rate is low (i.e., at a high reflux ratio) or when the column has a large number of stages between the top of the column and the reflux splitter 48. Removal of an overhead distillate during the time that heartcut is being withdrawn reduces the cycle time required for the distillation and improves maleic anhydride yield and throughput.

In a preferred embodiment, an overhead distillate enriched in low boilers is withdrawn via line 64 to purge middle boiling materials from the system and heartcut exits the column via line 46. The overhead vapor condensate leaving the separator 56 is entirely directed to the column as reflux. The weight ratio of reflux via line 54 to heartcut via line 46 is preferably between about 1.2:1 to about 4:1, more preferably between about 1.3:1 to about 3:1, and, most preferably between about 1.33:1 to about 2:1. The weight ratio of heartcut via line 46 to overhead distillate enriched in low boilers via line 64 is preferably between about 35:1 to about 210:1, more preferably between about 52:1 to about 174:1, and, most preferably between about 70:1 to about 140:1.

In another embodiment of the invention, overhead distillates are withdrawn via lines 60 and 64 to purge middle boiling materials from the system and heartcut exits the column via line 46. The weight ratio of reflux via line 54 to heartcut via line 46 is preferably between about 1.2:1 to about 4:1, more preferably between about 1.3:1 to about 3:1, and, most preferably between about 1.33:1 to about 2:1. The weight ratio of heartcut via line 46 to overhead distillates via lines 60 and 64 is preferably between about 35:1 to about 210:1, more preferably between about 52:1 to about 174:1, and, most preferably between about 70:1 to about 140:1.

In yet another embodiment, an overhead distillate is withdrawn via line 64 to purge middle boiling materials from the system and heartcut exits the column via line 60. No heartcut is removed via line 46.

The weight ratio of reflux via line 54 to heartcut via line 60 is preferably between about 0.2:1 to about 3:1, more preferably between about 0.3:1 to about 2:1, and, most preferably between about 0.33:1 to about 1:1. The weight ratio of heartcut via line 60 to overhead distillate enriched in low boilers via line 64 is preferably between about 35:1 to about 210:1, more preferably between about 52:1 to about 174:1, and, most preferably between about 70:1 to about 140:1.

The batch refiner 42 can include a reflux splitter 70 for removing a second forecut via line 72 as a first forecut via line 60 is withdrawn. A second forecut is removed from the stage at which the heartcut is withdrawn, or from a stage at which the temperature is not more than 10° C. lower than the temperature at the stage at which the heartcut is withdrawn. Removal of a second forecut improves maleic anhydride throughput and reduces the cycle time for the purification process. The weight ratio of the second forecut removed from the column to the remaining liquid travelling down the column from the stage at which the second forecut is removed is preferably between about 1:30 and about 1:2, more preferably between about 1:16 and about 1:4, and, most preferably, between about 1:10 and about 1:5.

At least one additional heartcut can also be withdrawn from the batch refiner 42 at a stage between the top of the column and the center stage. Removal of additional heartcut improves maleic anhydride throughput. Improved throughput may reduce the amount of polymerization that occurs in the still pot of the refiner 42 as a result of time/temperature exposure of the crude maleic anhydride for a prolonged time period.

After the heartcut is removed, the batch distillation is discontinued and the still pot is recharged with crude maleic anhydride. The contents of the batch refiner 42 drain into the still pot 44 during this shut down period. Once the still pot is recharged, the start up procedures detailed above can be commenced. The bottoms residue within the still pot 44 is periodically removed in order to expel polymers and tars which form as a result of thermal decomposition of components of the crude maleic anhydride.

Figure 2:
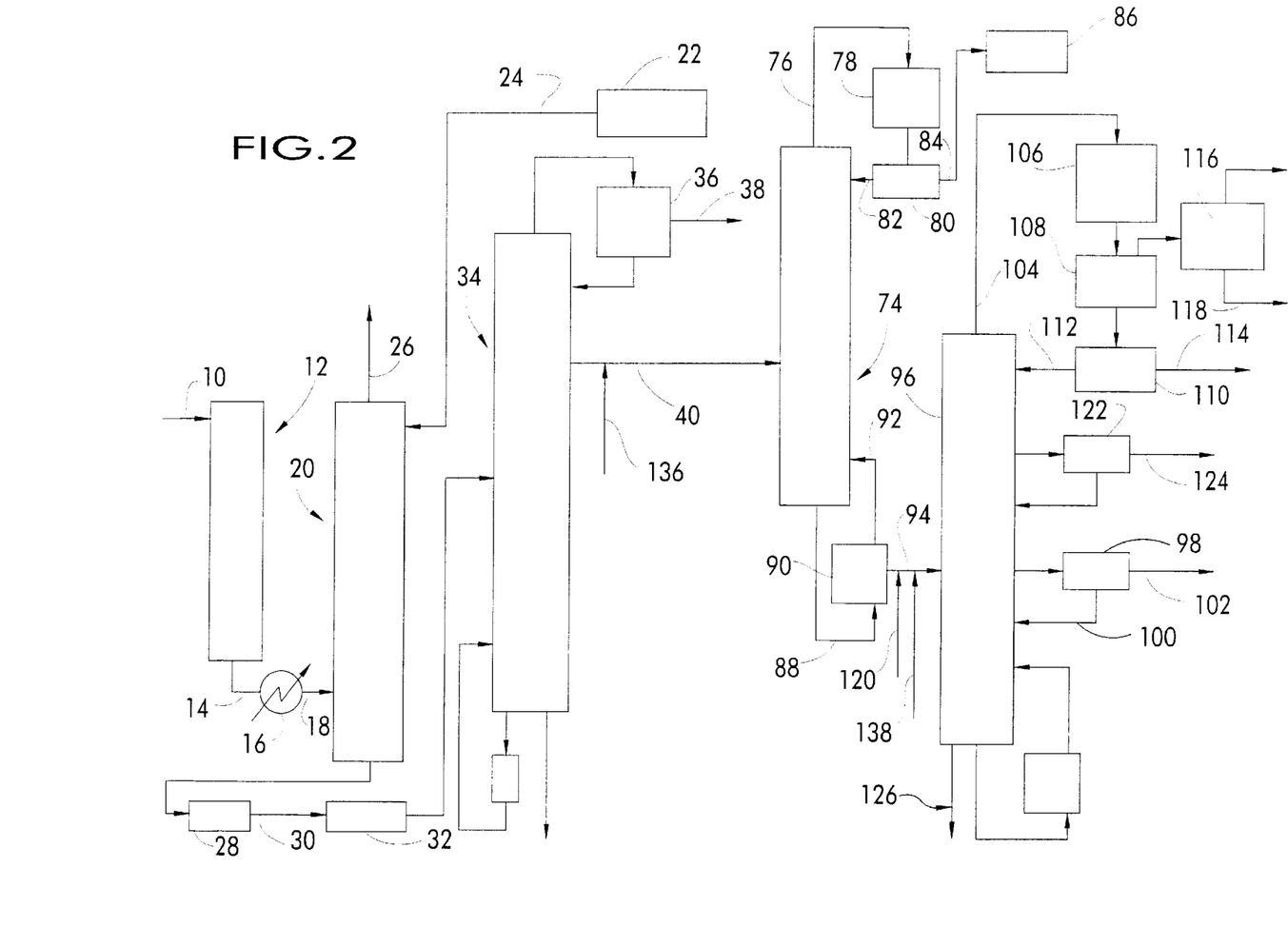
FIG. 2 is a schematic diagram of a process and apparatus for the purification and recovery of maleic anhydride via continuous distillation in accordance with the present invention.

In a continuous operation as shown in FIG. 2, crude maleic anhydride is directed via line 40 to an upper stage of a low boiler stripper 74 for removal of low boiling materials. Vapor rich in low boiling materials is removed from the top of the low boiler stripper via line 76 and condensed in a condenser 78 to form a low boiler stripper make. A reflux splitter 80 directs a portion of the low boiler stripper make to the column as reflux via line 82. The remainder of the low boiler stripper make is directed via line 84 to a storage tank 86. The low boiler stripper make from the storage tank 86 can be recycled to the lean solvent storage tank 22 storing the lean maleic anhydride absorbing solvent to be fed to the absorber column 20 or to the surge tank 28 storing the rich absorption liquor to be fed to the stripper column 34, or is purged from the system. The weight ratio of reflux via line 82 to remaining low boiler stripper make via line 84 is preferably between about 100:1 to about 1:1, more preferably between about 50:1 to about 5:1, and, most preferably between about 20:1 to about 10:1.

Liquid rich in middle and high boiling materials flows to the bottom of the stripper 74 and is directed via line 88 to a reboiler 90. Vapor from the reboiler 90 is returned to the low boiler stripper column via line 92. The bottoms liquid is also directed via line 94 to a continuous refiner 96 for separation of middle boiling materials from maleic anhydride in the liquid.

The low boiler stripper 74 is operated at a temperature which varies from between about 100° C. and about 180° C. in the reboiler to between about 115° C. and about 145° C. in the top vapor space. A temperature below about 115° C. at the top of the low boiler stripper 74 will not allow adequate purging of low boiling materials, and a temperature above about 145° C. at the top of the column may overload the condenser. The column is operated at a head pressure of about 50 to about 700 mm Hg. The volumetric rate of removal of low boiling material from the stripper 74 is between about 1% and about 20% of the volumetric rate of introduction of crude maleic anhydride into the column. Preferably, the volumetric rate of removal of low boiling material is between about 1% and about 10% of the volumetric rate of introduction of the crude maleic anhydride. If the volumetric rate of removal of low boiling material is greater than 20%, the maleic anhydride yield may be adversely effected.

In the continuous refiner 96, vapor is brought into countercurrent contact with a descending stream of boiling liquid. The concentration of middle boiling material in the vapor phase increases as the vapor rises toward the top of the column so long as the reflux to the column is richer in middle boiling materials than the equilibrium concentration corresponding to the vapor entering the column from the reboiler. At such conditions, some middle boiler diffuses from the liquid into the vapor. The heat of vaporization of the middle boiler is supplied by an equal amount of heat of condensation of high boiler as it diffuses from vapor to liquid. Thus, high boiler is transferred from vapor to liquid throughout the column, and a thermally equivalent amount of middle boiler is transferred from liquid to vapor. Middle boilers concentrate in the vapor at the top of the column, and high boilers concentrate in the liquid at the base of the column.

The continuous refiner 96 is a packed column or a tray column for promoting vapor/liquid contact and mass transfer of maleic anhydride from the vapor phase to the liquid phase. The refiner 96 generally includes between about 9 and about 40 equilibrium stages between the base of the column and a stage from which a side draw stream comprising maleic anhydride is withdrawn, and between about 1 and about 10 equilibrium stages between the stage from which the side draw stream is withdrawn and the top of the column. The operating temperature and pressure of the continuous refiner 96 are between about 125° C. and about 155° C., preferably between about 130° C. and about 140° C., and about 50 mm Hg to about 185 mm Hg, preferably between about 80 mm Hg and about 100 mm Hg.

A side draw stream comprising maleic anhydride is withdrawn at a stage above the center stage of the refiner 96. A liquid stream leaving the column enters a product splitter 98 that directs a portion of the liquid stream to the column as reflux via line 100. The remainder of the liquid stream is removed via line 102 as the side draw stream. In an alternative embodiment, the side draw stream is directly removed from the refiner 96 via line 102 without being directed through an external product splitter 98 because the liquid stream is split internally. In either embodiment, the weight ratio of the side draw stream withdrawn from the column to remaining liquid travelling down the column from the stage at which the side draw stream is withdrawn is preferably between about 3:1 and about 1:3, more preferably between about 2:1 and about 1:3, and, most preferably, between about 1:2 and about 1:3. At least one additional side draw stream can be withdrawn from the refiner 96 at a stage above the center stage of the column to improve maleic anhydride throughput.

As the side draw stream is withdrawn, an overhead vapor comprised of middle boiling materials, including maleic anhydride, having a boiling point between about 160° C. and about 285° C. at a pressure of 760 mm Hg is removed at a stage above that at which the side draw stream is withdrawn. Preferably, the overhead vapor is withdrawn at or near the top of the refiner 96 via line 104.

The overhead vapor is partially condensed in condenser 106 to form an overhead vapor condensate. The condensate separates from remaining vapor in a separator 108. A reflux splitter 110 directs a portion of the overhead vapor condensate to the column as reflux via line 112, while the remainder of the overhead vapor condensate is removed as an overhead distillate via line 114. The weight ratio of reflux via line 112 to overhead distillate via line 114 is preferably between about 20:1 to about 500:1, more preferably between about 50:1 to about 400:1, and, most preferably between about 70:1 to about 280:1.

The vapor leaving the separator 108 condenses in a condenser 116 and is removed as an overhead distillate enriched in low boilers via line 118. The overhead distillates can be recycled via lines 114 and 118 to the lean solvent storage tank 22 storing the lean maleic anhydride absorbing solvent to be fed to the absorber column 20, to the surge tank 28 storing the rich absorption liquor to be fed to the stripper column 34, or via line 120 to the crude maleic anhydride feed to the continuous refiner 96. The overhead distillate via line 114 can also be used as maleic anhydride product if the overhead product is of the desired purity and is heat stable.

The volumetric rate of removal of overhead distillates via lines 114 and 118 from the column is between about 1% and about 20% of the volumetric rate of introduction of crude maleic anhydride into the refiner 96. Preferably, the volume of overhead distillate removed is between about 1% and about 10% of the volumetric rate of introduction of crude maleic anhydride. If the volumetric rate of overhead distillate removed is greater than 20%, the maleic anhydride yield may be adversely effected.

The continuous process effectively separates middle boiling materials from maleic anhydride at the above-described reflux ratios to improve maleic anhydride yield and color stability. The maleic anhydride, acrylic acid and maleic acid content of the side draw stream is as described above for the heartcut of the batch distillation process.

The overhead distillates via lines 114 and 118 can be removed either continuously or intermittently. The overhead distillates via lines 114 and 118 are more concentrated in middle boiling materials when the overhead product flow rate is low (i.e., at a high reflux ratio) or when the column has many stages between the top of the column and the stage at which the side draw stream is withdrawn.

To most effectively separate middle boiling materials during fractionation, an overhead distillate is withdrawn via line 118 to purge middle boiling materials from the system, the side draw stream exits the column via line 102, and the overhead vapor condensate leaving the separator 108 is entirely directed to the column as reflux. The weight ratio of reflux via line 112 to side draw stream via line 102 is preferably between about 1.1:1 to about 4:1, more preferably between about 1.1:1 to about 2:1, and, most preferably between about 1.2:1 to about 1.5:1. The weight ratio of side draw stream via line 102 to overhead distillate via line 118 is preferably between about 20:1 to about 500:1, more preferably between about 50:1 to about 250:1, and, most preferably between about 100:1 to about 200:1.

In another embodiment of the invention, overhead distillates are withdrawn from refiner 96 via lines 114 and 118 to purge middle boiling materials from the system and a side draw stream exits the column via line 102. The weight ratio of reflux via line 112 to side draw stream via line 102 is preferably between about 1.1:1 to about 4:1, more preferably between about 1.1:1 to about 2:1, and, most preferably between about 1.2:1 to about 1.5:1. The weight ratio of side draw stream via line 102 to overhead distillate via line 114 is preferably between about 20:1 to about 500:1, more preferably between about 50:1 to about 250:1, and, most preferably between about 100:1 to about 200:1. The weight ratio of side draw stream via line 102 to overhead distillate enriched in low boilers via line 118 is preferably between about 20:1 to about 500:1, more preferably between about 50:1 to about 250:1, and, most preferably between about 100:1 to about 200:1.

In yet another embodiment, an overhead distillate is withdrawn via line 118 to purge middle boiling materials from the system and a product stream exits the column via line 114. No side draw stream is removed via line 102. The weight ratio of reflux via line 112 to product stream via line 114 is preferably between about 0.1:1 to about 3.1, more preferably between about 0.1:1 to about 1.1:1, and, most preferably between about 0.2:1 to about 0.5:1. The weight ratio of product stream via line 114 to overhead distillate via line 118 is preferably between about 20:1 to about 500:1, more preferably between about 50:1 to about 250:1, and, most preferably between about 100:1 to about 200:1.

The continuous refiner 96 can include a splitter 122 for removing a upper side draw stream via line 124. An upper side draw stream is removed from a stage at which the temperature is not more than 10° C. lower than the temperature at the stage at which the side is draw stream is withdrawn. Removal of an upper side draw stream improves maleic anhydride throughput and reduces the cycle time for the purification process. The weight ratio of the upper side draw stream removed from the column to the remaining liquid travelling down the column from the stage at which the upper side draw stream is removed is preferably between about 1:300 and about 1:20, more preferably between about 1:250 and about 1:50, and, most preferably, between about 1:200 and about 1:100.

Heavy ends materials having a higher boiling point than maleic anhydride are continuously removed from the refiner 96 via line 126.

The refined product withdrawn from the batch refiner 42 or the continuous refiner 96 is then treated with a stabilizer to provide a color stabilized maleic anhydride product. Conventional color stabilizers can be incorporated in the refined product, such as organic compounds with labile halogens and alkali metal halides as described in U.S. Pat. Nos. 3,903,117 and U.S. Pat. No. 3,775,436. The refined product has an HTH Hazen color of less than about 100, preferably less than about 50, and, more preferably, between about 15 and about 30. For purposes of the present invention, HTH Hazen color is determined by heating the maleic anhydride product at 180° C. for one hour and then measuring the color on the APHA scale.

In another embodiment of the present invention, the distillation of maleic anhydride is enhanced by treating crude maleic anhydride exiting the stripper column 34 with a sparge gas containing an inert gas and up to 5 mol. % oxygen, in order to purge low boiling materials and non-condensables from the crude maleic anhydride into the vapor within the column. It is believed that oxygen within a sparge gas oxidizes components that otherwise contribute to color formation and converts alcohol and aldehyde noncondensables to condensable acids. The oxygen concentration within the sparge gas does not exceed 5 mol. % to insure that the sparge gas is not flammable. The inert gas is selected from the group consisting of nitrogen, helium and argon. Preferably, the sparge gas comprises between about 95 mol. % and about 99 mol. % inert gas and between about 1 mol. % and about 5 mol. % oxygen.

In the batch distillation process illustrated in FIG. 1, crude maleic anhydride exits the stripper column 34 via line 40 and is introduced into still pot 44. The sparge gas is fed via line 128 into the incoming crude maleic anhydride feed, via line 130 directly into the still pot 44 above the surface of the crude maleic anhydride, via line 132 directly into the still pot below the surface of the crude maleic anhydride, or via line 134 directly into a lower stage of the refiner 42. Preferably, the sparge gas is introduced below the surface of the crude maleic anhydride within the still pot if the sparge gas contains oxygen. The ratio of millimoles of oxygen in the cumulative gas flow during distillation to moles of crude maleic anhydride initially charged to the refiner 42 is about 1.5:1 to about 1:1.7.

In the continuous distillation process illustrated in FIG. 2, crude maleic anhydride exits the stripper column 34 via line 40 and is introduced into the top of the low boiler stripper 74. The sparge gas is fed via line 136 into the incoming crude maleic anhydride feed to the stripper 74, and/or via line 138 into the partially purified maleic anhydride stream introduced via line 94 into the continuous refiner 96. The ratio of millimoles of oxygen in the feed to the stripper 74 or the continuous refiner 96 to moles of crude maleic anhydride in the feed to the stripper 74 or refiner 96 is about 3.5:1 to about 1:2.

The sparge gas is typically continuously added to the batch refiner or continuous fractionating column at a fixed rate throughout the fractionation. The sparge gas, however, can be introduced into the crude maleic anhydride before fractionation. The sparge can then be terminated before fractionation begins or can continue during fractionation.

The present invention is illustrated by the following examples which are merely for the purpose of illustration and are not to be regarded as limiting the scope of the invention or manner in which it may be practiced.

EXAMPLE 1

Crude maleic anhydride (3500 g) was fed to the still pot of a batch distillation column (hereinafter column A) comprised of a 20 tray oldershaw column below an automatic liquid dividing distillation splitter for withdrawal of maleic anhydride refined product, and a 5 tray Oldershaw column above the liquid dividing distillation splitter.

Overhead vapor was removed from the top of column A and condensed. A swinging bucket reflux splitter was used to remove a portion of the overhead vapor condensate as first forecut and to return the remainder of the overhead vapor condensate to column A as reflux. The first forecut removed from the column was 70 ml. The ratio of overhead vapor condensate returned as reflux to first forecut removed from column A was 10:1. Column A was operated at a still pot temperature of about 170° C. and a head pressure of about 285 mm Hg during forecut removal. An 80 ml second forecut was simultaneously withdrawn from the liquid dividing distillation splitter. The ratio of second forecut removed from column A to remaining liquid travelling down column A from the stage at which the second forecut is removed was 1:10.

Crude maleic anhydride (3500 g) was fed to the still pot of a batch distillation column (hereinafter column B) comprised of a 20 tray Oldershaw column below an automatic liquid dividing distillation splitter for withdrawal of maleic anhydride heartcut, and a 5 tray Oldershaw column above the liquid dividing distillation splitter. Vapor from the top of the column was condensed and the condensate was returned to the column as reflux. Column B was operated at a still pot temperature of about 170° C. and a head pressure of about 285 mm Hg. A nitrogen sparge was introduced into the still pot above the crude maleic anhydride at a rate of 0.6 mm nitrogen per mole of maleic anhydride. A 150 ml forecut was removed from the liquid dividing distillation splitter. The ratio of forecut removed from column B to remaining liquid travelling down column B from the stage at which the forecut is removed was 1:10.

Crude maleic anhydride (3500 g) was fed to the still pot of a batch distillation column (hereinafter column C) comprised of a 25 tray Oldershaw column below a tray Oldershaw column. A 150 ml overhead vapor was removed from the top of column C and condensed. A swinging bucket reflux splitter was used to remove a portion of the overhead vapor condensate as first forecut and to return the remainder of the overhead vapor condensate to column C as reflux. The first forecut removed from the column was 150 ml. The ratio of overhead vapor condensate returned as reflux to forecut removed from column C was 10:2. Column C was operated at a still pot temperature of about 170° C. and a head pressure of about 285 mm Hg during forecut removal.

The total impurities in the forecut samples were analyzed by capillary gas chromatography (GLPC). The total impurities for each forecut are reported below in Table 1:

TABLE 1

|  | Column A | Column B | Column C |
|---|---|---|---|
| First Forecut | 575 ppm | 804 ppm | 324 ppm |
| Second Forecut | 1813 ppm | — | — |

Column A removed 1.5 to 4 times the amount of impurities in the same forecut volume removed in columns B and C. The same source of crude maleic anhydride was used in columns A and B. The total impurities in the crude maleic anhydride fed to column C were found to be virtually identical to that fed to columns A and B. Therefore, the difference in the impurity levels is attributed to column configuration.

EXAMPLE 2

After removal of the forecut in column A, the still pot temperature and head pressure were reduced to 140° C. and 85 mm Hg, respectively. Eight 300 ml samples of heartcut were then withdrawn from the liquid dividing distillation splitter. The ratio of heartcut removed from column A to remaining liquid travelling down column A from the stage at which the heartcut is removed was 3:1.

During removal of the first three heartcut samples, a 33.3 ml overhead vapor was removed from the top of column A and condensed. The swinging bucket reflux splitter was used to return a portion of the overhead vapor condensate to column A as reflux. The remainder of the overhead vapor condensate was removed as an overhead distillate. The ratio of overhead vapor condensate returned as reflux to overhead distillate removed from column A was 12:1. The total impurities in the combined overhead vapor (100 ml) were 235 ppm.

After removal of the forecut in column B, the still pot temperature and head pressure were reduced to 140° C. and 85 mm Hg, respectively. Eight 300 ml samples of heartcut were then withdrawn from the liquid dividing distillation splitter. The ratio of heartcut removed from column B to remaining liquid travelling down column B from the stage at which the heartcut is removed was 3:1. No overhead vapor was taken from column B.

The total impurities and color stability of each heartcut sample are reported in Table 2 below. HT2 color stability testing was conducted by heating the sample to 140° C. for two hours. A more severe heat test, known as HTH testing, was completed by heating the sample to 180° C. for one hour. Color stability was measured using color comparator tubes (CPT) in which visual comparisons were made against an equal volume of a Pt-Co standard solution. Lovibond Colorscan PFX-990 instrument values (LVB) were determined as an alternative measure of color stability.

TABLE 2

| Heartcut sample[1] | Total impurities (ppm) | HT2-CPT (Hazen Color) | HT2-LVB (Hazen Color) | HTH-CPT (Hazen Color) | HTH-LVB (Hazen Color) |
|---|---|---|---|---|---|
| 1A | 54 | 20 | 16 | 140 | 113 |
| 1B | 124 | 24 | 23 | 350 | 218 |
| 2A | 41 | 18 | 11 | 190 | 137 |
| 2B | 86 | 20 | 17 | 350 | 199 |
| 3A | 50 | 16 | 10 | 100 | 80 |
| 3B | 59 | 18 | 12 | 130 | 98 |
| 4A | 52 | 12 | 10 | 200 | 143 |
| 4B | 54 | 20 | 15 | 300 | 174 |
| 5A | 52 | 12 | 10 | 60 | 51 |
| 5B | 29 | 14 | 9 | 350 | 199 |
| 6A | 41 | 14 | 12 | 130 | 92 |
| 6B | 65 | 14 | 8 | 140 | 104 |
| 7A | 64 | 18 | 15 | 80 | 64 |
| 7B | 75 | 14 | 8 | 210 | 142 |
| 8A[2] | — | — | — | — | — |
| 8B | 106 | 16 | 9 | 300 | 185 |

[1]A designates column A sample and B designates column B sample
[2]Mechanical problem caused loss of the sample.

Column A provided heartcut having enhanced color stability especially as measured in terms of HTH Hazen color, the more severe test for heat stability.

Samples 6 to 8 typically include more high-boiling, color-forming material resulting in higher HT2 Hazen color for these samples.

EXAMPLE 3

Crude maleic anhydride (2000 g) was fed to the still pot of a batch distillation column comprised of a 20 tray Oldershaw column below an automatic liquid dividing distillation splitter for withdrawal of maleic anhydride heartcut, and a 5 tray Oldershaw column above the liquid dividing distillation splitter.

A first run was made by removing both forecut and overhead distillate fractions from the column, hereinafter referred to as "forecut/overhead distillate run." Overhead vapor was removed from the top of the distillation column and condensed. An 80 ml condensate stream was removed from the column as forecut. The volume of forecut removed constituted 5% of the volume of the crude maleic anhydride introduced into the column. None of the overhead vapor condensate was returned to the column as reflux. The column was operated at a still pot temperature of about 170° C. and a head pressure of about 285 mm Hg during forecut removal. After removal of the forecut, the temperature and pressure were reduced to 140° C. and 85 mm Hg. Eight 150 ml samples of heartcut were then withdrawn from the liquid dividing distillation splitter. The ratio of heartcut removed from the column to remaining liquid travelling down the column from the stage at which the heartcut is removed was 3:1. During removal of the first five heartcut samples, a 100 ml overhead vapor was removed from the top of the column and condensed. The swinging bucket reflux splitter was used to return a portion of the overhead vapor condensate to the column as reflux. The remainder of the overhead vapor condensate was removed as an overhead distillate. The ratio of overhead vapor condensate returned as reflux to overhead distillate removed from the column was 10:1. The heartcuts were combined, stabilized, and analyzed for HT2 and HTH color stability using a Lovibond Colorscan. The heartcut composite had an HT2 Hazen color of 8 and an HTH Hazen color of 88.

A comparative run was made in which a larger volume of forecut is removed from the column without any overhead distillate removal, hereinafter referred to as an "extended forecut run." Overhead vapor was removed from the top of the distillation column and condensed. A 180 ml condensate stream was removed from the column as forecut. The forecut volume in the comparative run is equal to the combined volume of the forecut and overhead distillate fractions removed in the forecut/overhead distillate run described above. None of the overhead vapor condensate was returned to the column as reflux. The column was operated at a still pot temperature of about 170° C. and a head pressure of about 285 mm Hg during forecut removal. After removal of the forecut, the temperature and pressure were reduced to 140° C. and 85 mm Hg. Eight 150 ml samples of heartcut were then withdrawn from the liquid dividing distillation splitter. No overhead distillate fractions were taken. The heartcuts were combined, stabilized, and analyzed for HT2 and HTH color stability using Colorscan. The heartcut composite had an HT2 Hazen color of 9 and an HTH Hazen color of 160.

In order to determine the extent of run-to-run variation, eight additional runs were made, alternating the forecut/overhead distillate run and the extended forecut run as described above. The results are tabulated below in Table 3:

TABLE 3

| Run Type | HT2 (Hazen Color) | HTH (Hazen Color) |
|---|---|---|
| Forecut/overhead distillate | 15 | 30 |
| Extended forecut | 16 | 32 |
| Forecut/overhead distillate | 12 | 20 |
| Extended forecut | 12 | 70 |
| Forecut/overhead distillate | 19 | 34 |
| Extended forecut | 11 | 33 |
| Forecut/overhead distillate | 12 | 44 |
| Extended forecut | 10 | 29 |

The Hazen color of the samples is similar because the crude maleic anhydride contained only a small amount of impurities that decompose to form color formers. Crude maleic anhydride typically contains more of these impurities. Heartcut from typical crude maleic anhydride will exhibit improved color when a forecut and an overhead distillate are removed as compared to the color of heartcut when an extended forecut is removed. This improved color is illustrated in the first comparative runs of this example.

EXAMPLE 4

Crude maleic anhydride (2000 g) was fed to the still pot of a batch distillation column comprised of a 20 tray Oldershaw column below an automatic liquid dividing distillation splitter for withdrawal of maleic anhydride heartcut, and a 5 tray Oldershaw column above the liquid dividing distillation splitter.

An overhead vapor was removed from the top of the distillation column and condensed. A swinging bucket reflux splitter was used to return a portion of the overhead vapor condensate to the column as reflux. The ratio of overhead vapor condensate returned as reflux to first forecut removed from the column ranged between 15:1 and 1:1.8. A second forecut was removed from the liquid dividing distillation splitter during removal of the first forecut. The ratio of second forecut removed from the column to remaining liquid travelling down the column from the stage at which the second forecut is removed was between 1.7:1 and 1:15. The total forecut volume was between 40 ml and 215 ml. The column was operated at a still pot temperature of about 170° C. and a head pressure of about 285 mm Hg during forecut removal.

After removal of the forecut, the temperature and pressure were reduced to 140° C. and 85 mm Hg. Eight 150 ml samples of heartcut were then withdrawn from the liquid dividing distillation splitter. The ratio of heartcut removed from the column to remaining liquid travelling down the column from the stage at which the heartcut is removed was between 3:1 and 1:5. During removal of the first 2 to 4 heartcut samples, an overhead vapor was removed from the top of the column and condensed. The swinging bucket reflux splitter was used to return a portion of the overhead vapor condensate to the column as reflux. The remainder of the overhead vapor condensate was removed as an overhead distillate. The ratio of overhead vapor condensate returned as reflux to overhead distillate removed from the column during heartcut removal was between 20:1 and 2.7:1. The total volume of overhead distillate removed was between 40 ml and 110 ml. The heartcut fractions were combined, heated to 180° C. for one hour, and analyzed using Colorscan measurement to determine HTH Hazen color. The results of the study are shown in Table 4.

TABLE 4

| Run No. | FC/LS[1] | FC/US[2] | HC/LS[3] | HC/US[4] | Total Volume of Forecut Taken During Forecut Step (ml) | Total Volume of Overhead Distillate Taken During Heartcut Step (ml) | HTH Hazen Color |
|---|---|---|---|---|---|---|---|
| 1 | 1:1 | 1:1 | 1:5 | 5:1 | 200 | 100 | 191 |
| 2 | 15:1 | 1:1 | 1:5 | 20:1 | 200 | 50 | 225 |
| 3 | 1:1 | 15:1 | 1:5 | 20:1 | 50 | 100 | 245 |

TABLE 4-continued

| Run No. | FC/LS[1] | FC/US[2] | HC/LS[3] | HC/US[4] | Total Volume of Forecut Taken During Forecut Step (ml) | Total Volume of Overhead Distillate Taken During Heartcut Step (ml) | HTH Hazen Color |
|---|---|---|---|---|---|---|---|
| 4 | 15:1 | 15:1 | 1:5 | 5:1 | 50 | 50 | 288 |
| 5 | 1:1 | 1:1 | 2:1 | 20:1 | 50 | 50 | 203 |
| 6 | 15:1 | 1:1 | 2:1 | 5:1 | 50 | 100 | 80 |
| 7 | 1:1 | 15:1 | 2:1 | 5:1 | 200 | 50 | 79 |
| 8 | 15:1 | 15:1 | 2:1 | 20:1 | 200 | 100 | 177 |
| 9 | 3:3.5 | 4:1 | 3:1 | 4:1 | 40 | 110 | 200 |
| 10 | 3:3.5 | 3:3.5 | 3:1 | 12:1 | 190 | 110 | 91 |
| 11 | 4:1 | 3:3.5 | 3:1 | 4:1 | 190 | 60 | 21 |
| 12 | 1:1.7 | 1:1.3 | 2:1 | 6:1 | 155 | 90 | 18 |
| 13 | 1:1.7 | 1:1.3 | 2:1 | 6:1 | 155 | 90 | 23 |
| 14 | 1:1.6 | 1:1.8 | 2.8:1 | 3:1 | 215 | 65 | 50 |
| 15 | 1.5:1 | 1:1 | 1:1.6 | 2.7:1 | 160 | 40 | 26 |
| 16 | 1.3:1 | 1.2:1 | 1.4:1 | 4:1 | 140 | 75 | 29 |

[1]Forecut Step/Lower Splitter: Ratio of remaining liquid travelling down the column from the stage at which the second forecut is removed to second forecut removed from the column
[2]Forecut Step/Upper Splitter: Ratio of overhead vapor condensate returned as reflux to first forecut removed from the column
[3]Heartcut Step/Lower Splitter: Ratio of remaining liquid travelling down the column from the stage at which the heartcut is removed to heartcut removed from the column
[4]Heartcut Step/Upper Splitter: Ratio of overhead vapor condensate returned as reflux to overhead distillate removed from the column during heartcut removal The maleic anhydride heartcut of runs 11–16 exhibited a preferred HTH Hazen color not greater than 50, and the heartcut of runs 6, 7 and 10 exhibited a satisfactory HTH Hazen color less than 100.

In view of the above, it will be seen that the several objects of the invention are achieved.

As various changes could be made in the above-described invention without departing from its scope, it is intended that all matter contained in the above description be interpreted as illustrative and not in a limiting sense.

What is claimed:

1. A process for the purification of crude maleic anhydride by distillation, the process comprising: treating the crude maleic anhydride with a gas containing an inert gas and up to 5 mol. % oxygen such that noncondensables are purged from the crude maleic anhydride.

2. The process of claim 1 wherein the crude maleic anhydride is purified in a batch distillation column, the gas consists of an inert gas, and the inert gas is introduced either above or below the surface of the crude maleic anhydride within a still pot of the column.

3. The process of claim 1 wherein the crude maleic anhydride is purified in a batch distillation column, the gas comprises between about 95 mol. % and about 99 mol. % inert gas and between about 1 mol. % and about 5 mol. % oxygen, and the gas is introduced below the surface of the crude maleic anhydride within a still pot of the column.

4. The process of claim 1 wherein the crude maleic anhydride is purified in a continuous distillation column, and the gas comprises between about 95 mol. % and about 99 mol. % inert gas and between about 1 mol. % and about 5 mol. % oxygen.

5. The process of claim 1 wherein the inert gas is nitrogen, helium or argon.

6. The process of claim 1 wherein the noncondensables are purged from the crude maleic anhydride when the ratio of millimoles of oxygen in the cumulative gas flow during distillation to moles of crude maleic anhydride initially charged to the column is up to about 1.5:1.

7. The process of claim 6 wherein the gas comprises an inert gas and between about 0.6 and about 1.5 millimoles of oxygen per mole of crude maleic anhydride, and the gas is introduced below the surface of the crude maleic anhydride within a still pot of the column.

8. The process of claim 6 wherein the inert gas is nitrogen, helium or argon.

* * * * *